US008084478B2

(12) United States Patent
Butlin et al.

(10) Patent No.: US 8,084,478 B2
(45) Date of Patent: *Dec. 27, 2011

(54) SUBSTITUTED 5- PHENYLAMINO- 1, 3, 4-OXADIAZOL-2-YLCARBONYLAMINO-4-PHENOXY-CYCLOHEXANE CARBOXYLIC ACID AS INHIBITORS OF ACETYL COENZYME A DIACYLGLYCEROL ACYLTRANSFERASE

(75) Inventors: Roger John Butlin, Macclesfield (GB); Alleyn Thomas Plowright, Mölndal (SE)

(73) Assignee: AsstraZeneca AB, Sodertalje (SE)

( * ) Notice: Subject to any disclaimer, the term of this patent is extended or adjusted under 35 U.S.C. 154(b) by 79 days.

This patent is subject to a terminal disclaimer.

(21) Appl. No.: 12/302,185

(22) PCT Filed: May 29, 2007

(86) PCT No.: PCT/GB2007/001990
§ 371 (c)(1),
(2), (4) Date: Nov. 24, 2008

(87) PCT Pub. No.: WO2007/138311
PCT Pub. Date: Dec. 6, 2007

(65) Prior Publication Data
US 2009/0275620 A1 Nov. 5, 2009

Related U.S. Application Data

(60) Provisional application No. 60/809,298, filed on May 30, 2006.

(51) Int. Cl.
*A61K 31/4245* (2006.01)
*C07D 271/113* (2006.01)
(52) U.S. Cl. ......................................... 514/364; 548/143
(58) Field of Classification Search ........................ None
See application file for complete search history.

(56) References Cited

U.S. PATENT DOCUMENTS

| 4,983,731 | A | 1/1991 | Wagner et al. |
|---|---|---|---|
| 5,491,172 | A | 2/1996 | Lee et al. |
| 6,608,185 | B1 | 8/2003 | Omura et al. |
| 6,624,185 | B2 | 9/2003 | Glombik et al. |
| 7,138,414 | B2 | 11/2006 | Schoenafinger et al. |
| 7,453,010 | B2 | 11/2008 | Bovy et al. |
| 7,749,997 | B2 | 7/2010 | Birch et al. |
| 2002/0183384 | A1 | 12/2002 | Cornicelli et al. |
| 2003/0072757 | A1 | 4/2003 | Farese et al. |
| 2004/0102432 | A1 | 5/2004 | Sanganee et al. |
| 2005/0070545 | A1 | 3/2005 | Fox et al. |
| 2007/0123504 | A1 | 5/2007 | Bolin et al. |
| 2007/0155832 | A1 | 7/2007 | Haeberlein et al. |
| 2007/0249620 | A1 | 10/2007 | Kurata et al. |
| 2008/0090876 | A1 | 4/2008 | Cheng et al. |
| 2008/0096874 | A1* | 4/2008 | Birch et al. ............... 514/222.5 |
| 2008/0306059 | A1 | 12/2008 | Birch et al. |
| 2009/0048258 | A1 | 2/2009 | Ogino et al. |
| 2009/0093497 | A1 | 4/2009 | Bolin et al. |
| 2009/0197926 | A1 | 8/2009 | Birch et al. |
| 2009/0209602 | A1 | 8/2009 | Butlin et al. |
| 2009/0215779 | A1 | 8/2009 | Butlin et al. |
| 2009/0298853 | A1 | 12/2009 | Bauer et al. |
| 2010/0029727 | A1 | 2/2010 | Johnstone et al. |
| 2010/0160397 | A1 | 6/2010 | Birch et al. |
| 2010/0173958 | A1 | 7/2010 | Bennett et al. |
| 2010/0184813 | A1 | 7/2010 | Birch et al. |

FOREIGN PATENT DOCUMENTS

| DE | 10223273 | 12/2003 |
|---|---|---|
| EP | 1236468 | 9/2002 |
| JP | 2004/067635 | 3/2004 |
| JP | 2005/206492 | 8/2005 |
| JP | 2007/131584 | 5/2007 |
| JP | 2007/191471 | 8/2007 |
| WO | WO 94/26702 | 11/1994 |
| WO | WO 00/58491 | 10/2000 |
| WO | WO 02/20484 | 3/2002 |
| WO | WO 03/099772 | 12/2003 |
| WO | WO 2004/007455 | 1/2004 |
| WO | WO 2004/047755 | 6/2004 |

(Continued)

OTHER PUBLICATIONS

Patani et al. "Bioisosterism: A Rational Approach in Drug Design." Chem Rev. 1996, 96, 3147-3176.*
Adcock et al., "Electronic effect of the tricyanomethyl group by carbon-13 and fluorine-19 NMR: nature of aryl fluorine-19 NMR polar field effects in the benzene and naphthalene ring systems" Journal of Organic Chemistry 44 (17): 3004-3017 (1979).

(Continued)

*Primary Examiner* — Rebecca Anderson
*Assistant Examiner* — Alicia L Otton
(74) *Attorney, Agent, or Firm* — Morgan Lewis & Bockius LLP

(57) ABSTRACT

Compounds of formula (I), or salts thereof, which inhibit acetyl CoA (acetyl coenzyme A):diacylglycerol acyltransferase (DGAT1) activity are provided, (I)

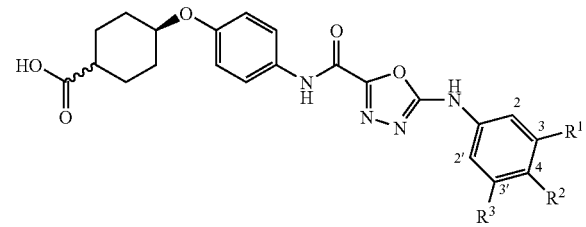

wherein $R^1$, $R^2$ and $R^3$ are each independently selected from hydrogen, fluoro, chloro, cyano, trifluoromethyl, trifluoromethoxy and difluoromethoxy; together with processes for their preparation, pharmaceutical compositions containing them and their use as medicaments.

13 Claims, No Drawings

FOREIGN PATENT DOCUMENTS

| WO | WO 2004/100881 | 11/2004 |
|---|---|---|
| WO | WO 2005/013907 | 2/2005 |
| WO | WO 2005/044250 | 5/2005 |
| WO | WO 2005/046670 | 5/2005 |
| WO | WO 2005/072740 | 8/2005 |
| WO | WO 2006/004200 | 1/2006 |
| WO | WO 2006/019020 | 2/2006 |
| WO | WO 2006/044775 | 4/2006 |
| WO | WO 2006/064189 * | 6/2006 |
| WO | WO 2006/082010 | 8/2006 |
| WO | WO 2006/082952 | 8/2006 |
| WO | WO 2006/113919 | 10/2006 |
| WO | WO 2006/120125 | 11/2006 |
| WO | WO 2006/134317 | 12/2006 |
| WO | WO 2007/016538 | 2/2007 |
| WO | WO 2007/060140 | 5/2007 |
| WO | WO 2007/071966 | 6/2007 |
| WO | WO 2007/126957 | 11/2007 |
| WO | WO 2007/137103 | 11/2007 |
| WO | WO 2007/137107 | 11/2007 |
| WO | WO 2007/138304 | 12/2007 |
| WO | WO 2007/141502 | 12/2007 |
| WO | WO 2007/141517 | 12/2007 |
| WO | WO 2007/141538 | 12/2007 |
| WO | WO 2007/141545 | 12/2007 |
| WO | WO 2007/144571 | 12/2007 |
| WO | WO 2008/011130 | 1/2008 |
| WO | WO 2008/011131 | 1/2008 |
| WO | WO 2008/039007 | 4/2008 |
| WO | WO 2008/039008 | 4/2008 |
| WO | WO 2008/040651 | 4/2008 |
| WO | WO 2008/048991 | 4/2008 |
| WO | WO 2008/067257 | 6/2008 |
| WO | WO 2008/099221 | 8/2008 |
| WO | WO 2008/129319 | 10/2008 |
| WO | WO 2008/134690 | 11/2008 |
| WO | WO 2008/134693 | 11/2008 |
| WO | WO 2008/141976 | 11/2008 |
| WO | WO 2008/148840 | 12/2008 |
| WO | WO 2008/148849 | 12/2008 |
| WO | WO 2008/148851 | 12/2008 |
| WO | WO 2008/148868 | 12/2008 |
| WO | WO 2009/011285 | 1/2009 |
| WO | WO 2009/016462 | 2/2009 |
| WO | WO 2009/024821 | 2/2009 |
| WO | WO 2009/037222 | 3/2009 |
| WO | WO 2009/040410 | 4/2009 |
| WO | WO 2009/071483 | 6/2009 |
| WO | WO 2009/081195 | 7/2009 |
| WO | WO 2009/112445 | 9/2009 |

OTHER PUBLICATIONS

Anderson et al. "Identification of a Form of Acyl-CoA:Cholesterol Acyltransferase Specific to Liver and Intestine in Nonhuman Primates" J Biol Chem 273(41):26747-26754 (1998).

Birch et al. "Discovery of a Potent, Selective, and Orally Efficacious Pyrimidinooxazinyl Bicyclooctaneacetic Acid Diacylglycerol Acyltransferase-1 Inhibitor" J. Med. Chem. 52(6):1558-1568 (2009).

Brown and Goldstein "Lipoprotein metabolism in the macrophage: implications for cholesterol deposition in atherosclerosis" Annu Rev Biochem. 52:223-261 (1983).

Burnett and Huff "Avasimibe Pfizer" Curr Opin Investig Drugs 3(9):1328-1333 (2002).

CAPLUS RN 404032-15-1, retrieved from CAPLUS on Jul. 17, 2009.

Cases et al. "ACAT-2, A Second Mammalian Acyl-CoA:Cholesterol Acyltransferase" J Biol Chem 273(41):26755-26764 (1998).

Cases et al. "Cloning of DGAT2, a Second Mammalian Diacylglycerol Acyltransferase, and Related Family Members" J. Biol. Chem. 276(42):38870-38876 (2001).

Cases et al. "Identification of a gene encoding an acyl CoA:diacylglycerol acyltransferase, a key enzyme in triacylglycerol synthesis" Proc Natl Acad Sci U S A. 95(22):13018-13023 (1998).

Chang et al. "Molecular cloning and functional expression of human acyl-coenzyme A:cholesterol acyltransferase cDNA in mutant Chinese hamster ovary cells" J. Biol. Chem. 268(28):20747-20755 (1993).

Chen et al. "Increased Insulin and Leptin Sensitivity in Mice Lacking ACYL COA: Diacylglycerol Acyltransferase 1" Journal of Clinical Investigation 109(8):1049-1055 (2002).

Chen et al. "Inhibition of Triglyceride Synthesis as a Treatment Strategy for Obesity: Lessons From DGAT1-Deficient Mice" Arteriosclerosis, Thrombosis, and Vascular Biology 25(3): 482-486 (2005).

Chen et al. "Obesity resistance and enhanced glucose metabolismin mice transplanted with white adipose tissue lacking acyl CoA:diacylglycerol acyltransferase 1" J. Clin. Invest. 111(11):1715-1722 (2003).

Coleman "Diacylglycerol acyltransferase and monoacylglycerol acyltransferase from liver and intestine" Methods in Enzymology 209:98-104 (1992).

Field and Salome "Effect of dietary fat saturation, cholesterol and cholestyramine on acyl-CoA: cholesterol acyltransferase activity in rabbit intestinal microsomes" Biochimica et Biophysica Acta 712(3):557-570 (1982).

Hoffman et al. "Synthesis and evaluation of 2-pyridinone derivatives as HIV-1-specific reverse transcriptase inhibitors. 4. 3-[2-(Benzoxazol-2-yl)ethyl]-5-ethyl-6-methylpyridin-2(1H)-one and analogs" Journal of Medicinal Chemistry 36(8):953-966 (1993).

Hubbard et al. "Antisense and small-molecule modulation of diacylglycerol acyltransferase" Expert Opinion on Therapeutic Patents 17(11): 1331-1339 (2007).

Insull Jr. et al. "Efficacy and short-term safety of a new ACAT inhibitor, avasimibe, on lipids, lipoproteins, and apolipoproteins, in patients with combined hyperlipidemia" Atherosclerosis 157(1):137-144 (2001).

Lehner and Kuksis "Biosynthesis of triacylglycerols" Prog Lipid Res. 35(2):169-201 (1996).

Oelkers et al. "Characterization of Two Human Genes Encoding Acyl Coenzyme A:Cholesterol Acyltransferase-related Enzymes" J Biol Chem 273(41):26765-26771 (1998).

Robertson et al. "Preclinical Safety Evaluation of Avasimibe in Beagle Dogs: An ACAT Inhibitor with Minimal Adrenal Effects" Toxicological Sciences 2001 US, 59(2):324-334 (2001).

Sawhney et al. "Synthesis of some 2-(5-substituted 1,3,4-oxadiazol-2-yl)-, 2-(5-substituted 1,3,4-thiadiazol-2-y1)- and 2-(3-mercapto-4-substituted-4H-1,2,4-triazol-5 -yl)- benzimidazoles as potential antiinflammatory agents" Indian Journal of Chemistry Section B, 30B:407-412 (1991).

Smith et al. "Obesity resistance and multiple mechanisms of triglyceride synthesis in mice lacking Dgat" Nature Genetics 25:87-90 (2000).

Yen et al. "Identification of a gene encoding MGAT1, a monoacylglycerol acyltransferase" Proc Natl Acad Sci U S A. 99(13):8512-8517 (2002).

Yen et al. "Thematic Review Series: Glycerolipids. DGAT enzymes and triacylglycerol biosynthesis" Journal of Lipid Research 49: 2283-2301 (2008).

Zammit et al. "Diacylglycerol acyltransferases: Potential roles as pharmacological targets" Pharmacology & Therapeutics 118(3):295-302 (2008).

Zhao et al. "Validation of diacyl glycerolacyltransferase I as a novel target for the treatment of obesity and dyslipidemia using a potent and selective small molecule inhibitor" J. Med. Chem. 51:380-383 (2008).

Birch et al. "DGAT1 inhibitors as anti-obesity and anti-diabetic agents" Current Opinion in Drug Discovery and Development 13(4):489-96 (Jul. 2010).

Database Crossfire Beilstein, Beilstein-Institut zur Förderung der Chemischen Wissenschaften, Frankfurt, AM Main, DE; Database Accession No. 2395704 (BRN), XP002512066, 2008.

* cited by examiner

SUBSTITUTED 5- PHENYLAMINO- 1, 3, 4-OXADIAZOL-2-YLCARBONYLAMINO-4-PHENOXY-CYCLOHEXANE CARBOXYLIC ACID AS INHIBITORS OF ACETYL COENZYME A DIACYLGLYCEROL ACYLTRANSFERASE

RELATED APPLICATIONS

The present application is a U.S. National Phase Application of International Application No. PCT/GB2007/001990 (filed May 29, 2007) which claims the benefit of U.S. Provisional Application No. 60/809,298 (filed May 30, 2006), both of which are hereby incorporated by reference in their entirety.

The present invention relates to compounds which inhibit acetyl CoA (acetyl coenzyme A):diacylglycerol acyltransferase (DGAT1) activity, processes for their preparation, pharmaceutical compositions containing them as the active ingredient, methods for the treatment of disease states associated with DGAT1 activity, to their use as medicaments and to their use in the manufacture of medicaments for use in the inhibition of DGAT1 in warm-blooded animals such as humans. In particular this invention relates to compounds useful for the treatment of type II diabetes, insulin resistance, impaired glucose tolerance and obesity in warm-blooded animals such as humans, more particularly to the use of these compounds in the manufacture of medicaments for use in the treatment of type II diabetes, insulin resistance, impaired glucose tolerance and obesity in warm-blooded animals such as humans.

Acyl CoA:diacylglycerol acyltransferase (DGAT) is found in the microsomal fraction of cells. It catalyzes the final reaction in the glycerol phosphate pathway, considered to be the main pathway of triglyceride synthesis in cells by facilitating the joining of a diacylglycerol with a fatty acyl CoA, resulting in the formation of triglyceride. Although it is unclear whether DGAT is rate-limiting for triglyceride synthesis, it catalyzes the only step in the pathway that is committed to producing this type of molecule [Lehner & Kuksis (1996) Biosynthesis of triacylglycerols. Prog. Lipid Res. 35: 169-201].

Two DGAT genes have been cloned and characterised. Both of the encoded proteins catalyse the same reaction although they share no sequence homology. The DGAT1 gene was identified from sequence database searches because of its similarity to acyl CoA:cholesterol acyltransferase (ACAT) genes. [Cases et al (1998) Identification of a gene encoding an acyl CoA:diacylglycerol acyltransferase, a key enzyme in triacylglycerol synthesis. Proc. Natl. Acad. Sci. USA 95: 13018-13023]. DGAT1 activity has been found in many mammalian tissues, including adipocytes.

Because of the previous lack of molecular probes, little is known about the regulation of DGAT1. DGAT1 is known to be significantly up-regulated during adipocyte differentiation.

Studies in gene knockout mice has indicated that modulators of the activity of DGAT1 would be of value in the treatment of type II diabetes and obesity. DGAT1 knockout (Dgat1$^{-/-}$) mice, are viable and capable of synthesizing triglycerides, as evidenced by normal fasting serum triglyceride levels and normal adipose tissue composition. Dgat1$^{-/-}$ mice have less adipose tissue than wild-type mice at baseline and are resistant to diet-induced obesity. Metabolic rate is ~20% higher in Dgat1$^{-/-}$ mice than in wild-type mice on both regular and high-fat diets [Smith et al (2000) Obesity resistance and multiple mechanisms of triglyceride synthesis in mice lacking DGAT. Nature Genetics 25: 87-90]. Increased physical activity in Dgat1$^{-/-}$ mice partially accounts for their increased energy expenditure. The Dgat1$^{-/-}$ mice also exhibit increased insulin sensitivity and a 20% increase in glucose disposal rate. Leptin levels are 50% decreased in the Dgat1$^{-/-}$ mice in line with the 50% decrease in fat mass.

When Dgat1$^{-/-}$ mice are crossed with ob/ob mice, these mice exhibit the ob/ob phenotype [Chen et al (2002) Increased insulin and leptin sensitivity in mice lacking acyl CoA:diacylglycerol acyltransferase J. Clin. Invest. 109:1049-1055] indicating that the Dgat1$^{-/-}$ phenotype requires an intact leptin pathway. When Dgat1$^{-/-}$ mice are crossed with Agouti mice a decrease in body weight is seen with normal glucose levels and 70% reduced insulin levels compared to wild type, agouti or ob/ob/Dgat1$^{-/-}$ mice.

Transplantation of adipose tissue from Dgat1$^{-/-}$ mice to wild type mice confers resistance to diet-induced obesity and improved glucose metabolism in these mice [Chen et al (2003) Obesity resistance and enhanced glucose metabolism in mice transplanted with white adipose tissue lacking acyl CoA:diacylglycerol acyltransferase J. Clin. Invest. 111: 1715-1722].

International Patent Applications WO2004/047755 (Tularik and Japan Tobacco) and WO2005/013907 (Japan Tobacco and Amgen) describe fused bicyclic nitrogen-containing heterocycles which are inhibitors of DGAT-1. JP2004-67635 (Otsuka Pharmaceuticals) describes thiazoleamido substituted phenyl compounds which are further substituted with alkylphosphonates and which inhibit DGAT-1. WO2004/100881 (Bayer) describes biphenylamino compounds substituted with imidazole, oxazole or thiazole which inhibit DGAT-1.

Our co-pending International Application PCT/GB2005/004726 describes oxadiazole compounds which inhibit DGAT-1, including two compounds similar to the compounds of formula (I) below. Some of the compounds in PCT/GB2005/004726 also show activity against the ACAT enzyme.

Accordingly, the present invention provides a compound of formula (I)

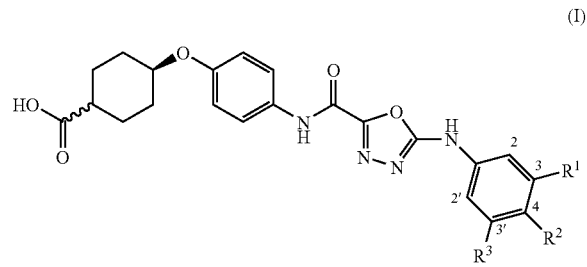

or a salt thereof, wherein:
$R^1$, $R^2$ and $R^3$ are each independently selected from hydrogen, methyl, ethyl, methoxy, ethoxy, fluoro, chloro, cyano, trifluoromethyl, trifluoromethoxy and difluoromethoxy.

We have found that, in compounds such as those of formula (I) above, the absence of a substituent at the 2 and 2' positions of the phenyl ring, as indicated above, generally leads to improved selectivity over the ACAT enzyme compared to compounds with a substituent at either the 2 or 2' position.

It will be appreciated that formula (I) includes compounds wherein the carboxy group and the oxy link are in either a cis or a trans arrangement across the cyclohexyl ring, in relation to each other.

In this specification the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1-10 carbon atoms, suitably from 1-6 carbon atoms, preferably 1-4 carbon atoms.

In this specification the term "alkoxy" means an alkyl group as defined hereinbefore linked to an oxygen atom.

For the avoidance of doubt it is to be understood that where in this specification a group is qualified by 'hereinbefore defined' or 'defined hereinbefore' the said group encompasses the first occurring and broadest definition as well as each and all of the particular definitions for that group.

If not stated elsewhere, suitable optional substituents for a particular group are those as stated for similar groups herein.

A compound of formula (I) may form stable acid or basic salts, and in such cases administration of a compound as a salt may be appropriate, and pharmaceutically acceptable salts may be made by conventional methods such as those described following.

Suitable pharmaceutically-acceptable salts include acid addition salts such as methanesulfonate, tosylate, α-glycerophosphate, fumarate, hydrochloride, citrate, maleate, tartrate and (less preferably) hydrobromide. Also suitable are salts formed with phosphoric and sulfuric acid. In another aspect suitable salts are base salts such as Group (I) (alkali metal) salt, Group (II) (alkaline earth) metal salt, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions.

However, to facilitate isolation of the salt during preparation, salts which are less soluble in the chosen solvent may be preferred whether pharmaceutically-acceptable or not.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which inhibits DGAT1 activity and is not to be limited merely to any one tautomeric form utilised within the formulae drawings.

Pro-drugs of compounds of formula (I), and salts thereof, are also within the scope of the invention.

Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and
H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984).

Examples of such prodrugs are in vivo cleavable esters of a compound of the invention. An in vivo cleavable ester of a compound of the invention containing a carboxy group is, for example, a pharmaceutically-acceptable ester which is cleaved in the human or animal body to produce the parent acid. Suitable pharmaceutically-acceptable esters for carboxy include (1-6C)alkyl esters, for example methyl or ethyl; (1-6C)alkoxymethyl esters, for example methoxymethyl; (1-6C)alkanoyloxymethyl esters, for example pivaloyloxymethyl; phthalidyl esters; (3-8C)cycloalkoxycarbonyloxy(1-6C)alkyl esters, for example 1-cyclohexylcarbonyloxyethyl; 1,3-dioxolan-2-ylmethyl esters, for example 5-methyl-1,3-dioxolan-2-ylmethyl; (1-6C)alkoxycarbonyloxyethyl esters, for example 1-methoxycarbonyloxyethyl; aminocarbonylmethyl esters and mono- or di-N-((1-6C)alkyl) versions thereof, for example N,N-dimethylaminocarbonylmethyl esters and N-ethylaminocarbonylmethyl esters; and may be formed at any carboxy group in the compounds of this invention. An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include (1-6C)alkanoyl esters, for example acetyl esters; and benzoyl esters wherein the phenyl group may be substituted with aminomethyl or N-substituted mono- or di-(1-6C)alkyl aminomethyl, for example 4-aminomethylbenzoyl esters and 4-N,N-dimethylaminomethylbenzoyl esters.

It will be appreciated by those skilled in the art that certain compounds of formula (I) contain asymmetrically substituted carbon and/or sulfur atoms, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the inhibition of DGAT1 activity, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy for the inhibition of DGAT1 activity by the standard tests described hereinafter.

It is also to be understood that certain compounds of the formula (I) and salts thereof can exist in solvated as well as unsolvated forms such as, for example, hydrated forms. It is to be understood that the invention encompasses all such solvated forms which inhibit DGAT1 activity.

As stated before, we have discovered a range of compounds that have good DGAT1 inhibitory activity. They have good physical and/or pharmacokinetic properties in general. The following compounds possess preferred pharmaceutical and/or physical and/or pharmacokinetic properties.

In one aspect, the carboxy group and oxy links are in a cis configuration across the cyclohexyl ring, to give a compound of formula (IA):

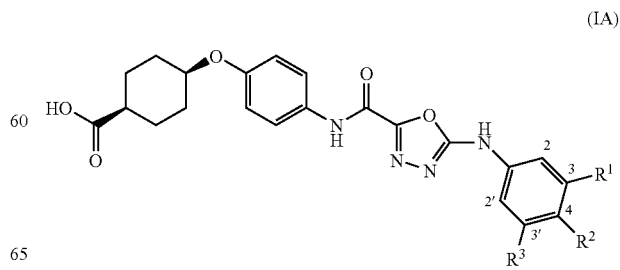

In another aspect, the carboxy group and oxy links are in a trans configuration across the cyclohexyl ring, to give a compound of formula (IB):

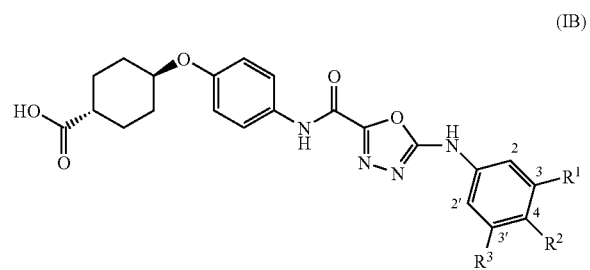

(IB)

References hereinbefore or hereinafter to a compound of formula (I) should be taken to apply also to compounds of formulae (IA) and (IB).

In one embodiment of the invention there are provided compounds of formulae (I), (IA) and (IB), in an alternative embodiment there are provided salts, particularly pharmaceutically-acceptable salts of compounds of formulae (I), (IA) and (IB). In a further embodiment, there are provided pro-drugs, particularly in-vivo cleavable esters, of compounds of formulae (I), (IA) and (IB). In a further embodiment, there are provided salts, particularly pharmaceutically-acceptable salts of pro-drugs of compounds of formulae (I), (IA) and (IB). Particular values of substituents in compounds of formulae (I), (IA) and (IB) are as follows. Such values may be used where appropriate with any of the other values, definitions, claims or embodiments defined hereinbefore or hereinafter.

1) $R^2$ is selected from fluoro, chloro, cyano, trifluoromethyl, trifluoromethoxy and difluoromethoxy.
2) $R^2$ is selected from fluoro, chloro, trifluoromethyl, trifluoromethoxy and difluoromethoxy.
3) $R^2$ is fluoro, difluoromethoxy or trifluoromethoxy, preferably fluoro.
4) $R^2$ is fluoro or chloro, preferably fluoro.
5) if $R^2$ is cyano then at least one of $R^1$ and $R^3$ is not hydrogen.
6) $R^1$ is hydrogen or fluoro.
7) $R^3$ is hydrogen or fluoro.
8) $R^2$ is fluoro and $R^1$ and $R^3$ are each independently hydrogen or fluoro.

Further preferred compounds of the invention are each of the Examples, each of which provides a further independent aspect of the invention. In further aspects, the present invention also comprises any two or more compounds of the Examples.

In a further aspect, the present invention comprises any one or more of the following, or salts thereof:

cis-4-{4-[({5-[(3,4-difluorophenyl)amino]-1,3,4-oxadiazol-2-yl}carbonyl)amino]-phenoxy}cyclohexanecarboxylic acid;

cis-4-{4-[({5-[(3-chloro-4-cyanophenyl)amino]-1,3,4-oxadiazol-2-yl}carbonyl)amino] phenoxy}cyclohexanecarboxylic acid;

cis-4-(4-{[(5-{[4-(trifluoromethoxy)phenyl]amino}-1,3,4-oxadiazol-2-yl)carbonyl]amino}phenoxy)cyclohexanecarboxylic acid;

cis-4-(4-{[(5-{[3-fluoro-5-(trifluoromethyl)phenyl]amino}-1,3,4-oxadiazol-2-yl)carbonyl]amino}phenoxy)cyclohexanecarboxylic acid;

cis-4-{4-[({5-[(3,4,5-trifluorophenyl)amino]-1,3,4-oxadiazol-2-yl}carbonyl)amino] phenoxy}cyclohexanecarboxylic acid;

cis-4-{4-[({5-[(4-cyanophenyl)amino]-1,3,4-oxadiazol-2-yl}carbonyl)amino]phenoxy}cyclohexanecarboxylic acid;

cis-4-{4-[({5-[(4-fluorophenyl)amino]-1,3,4-oxadiazol-2-yl}carbonyl)amino]phenoxy}cyclohexanecarboxylic acid;

cis-4-(4-{[(5-{[4-cyano-3-(trifluoromethyl)phenyl]amino}-1,3,4-oxadiazol-2-yl)carbonyl]amino}phenoxy)cyclohexanecarboxylic acid;

cis-4-(4-{[(5-{[3-(difluoromethoxy)phenyl]amino}-1,3,4-oxadiazol-2-yl)carbonyl]amino}phenoxy)cyclohexanecarboxylic acid;

cis-4-(4-{[(5-{[4-(difluoromethoxy)phenyl]amino}-1,3,4-oxadiazol-2-yl)carbonyl]amino}phenoxy)cyclohexanecarboxylic acid;

cis-4-{4-[({5-[(3-cyanophenyl)amino]-1,3,4-oxadiazol-2-yl}carbonyl)amino]phenoxy}cyclohexanecarboxylic acid;

trans-4-(4-{[(5-{[4-(difluoromethoxy)phenyl]amino}-1,3,4-oxadiazol-2-yl)carbonyl]-amino}phenoxy)cyclohexanecarboxylic acid;

trans-4-{4-[({5-[(4-fluorophenyl)amino]-1,3,4-oxadiazol-2-yl}carbonyl)amino]phenoxy}cyclohexanecarboxylic acid;

trans-4-{4-[({5-[(3-cyanophenyl)amino]-1,3,4-oxadiazol-2-yl}carbonyl)amino]phenoxy}cyclohexanecarboxylic acid;

trans-4-{4-[({5-[(4-cyanophenyl)amino]-1,3,4-oxadiazol-2-yl}carbonyl)amino]phenoxy}cyclohexanecarboxylic acid;

trans-4-(4-{[(5-{[4-(trifluoromethoxy)phenyl]amino}-1,3,4-oxadiazol-2-yl)carbonyl]amino}phenoxy)cyclohexanecarboxylic acid; and trans-4-{4-[({5-[(3,4-difluorophenyl)amino]-1,3,4-oxadiazol-2-yl}carbonyl)amino] phenoxy}cyclohexanecarboxylic acid.

Process

A compound of formula (I) and its salts may be prepared by any process known to be applicable to the preparation of chemically related compounds. Such processes, when used to prepare a compound of the formula (I), or a pharmaceutically-acceptable salt thereof, are provided as a further feature of the invention.

In a further aspect the present invention also provides that the compounds of the formula (I) and salts thereof, can be prepared by a process a) to b) as follows (wherein all variables are as hereinbefore defined for a compound of formula (I) unless otherwise stated):

a) reaction of an amine of formula (2) with a carboxylate salt of formula (3), wherein R is (1-6C)alkyl (for example methyl, ethyl, isopropyl and tert-butyl) followed by hydrolysis of the R group;

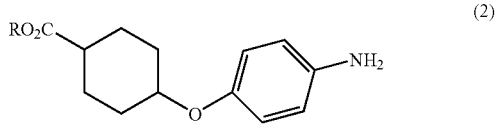

(2)

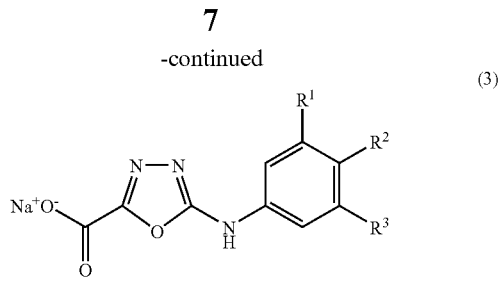

(3)

b) cyclisation of a compound of formula (4) (where X is S or O) wherein R is (1-6C)alkyl, followed by hydrolysis of the R group;

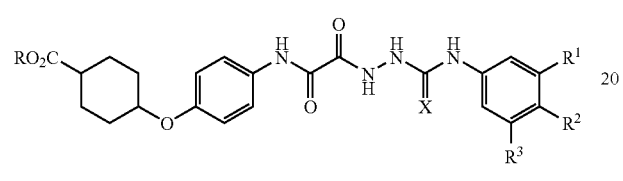

(4)

and thereafter if necessary:
1) removing any protecting groups; and/or
2) forming a salt.

Process a)

Compounds of formula (2) may be made by application of standard synthetic methods well known in the art. In particular, compounds of formula (2) may be prepared by reduction of a compound of formula (2A).

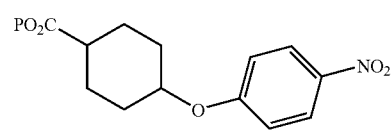

(2A)

Compounds of formula (2A) may be made by $S_NAr$ chemistry as illustrated in Scheme 1, wherein R is a (1-6C)alkyl group and X is for example fluoro:

Scheme 1

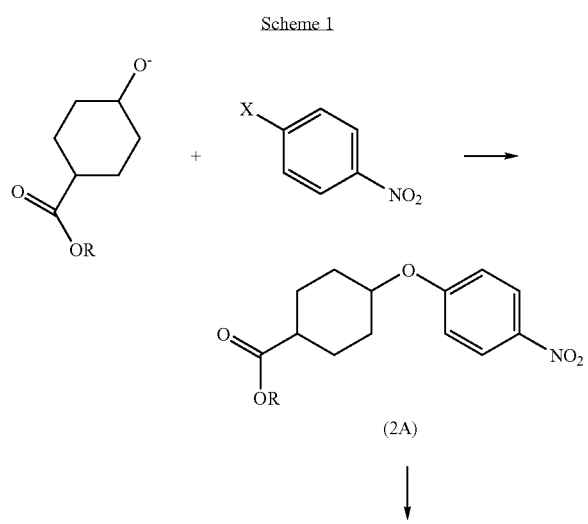

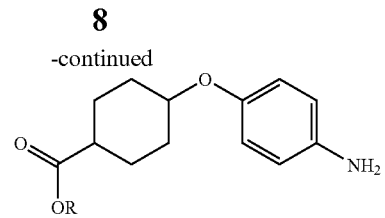

(2)

Compounds of formula (3) may be made by alkaline hydrolysis of ester (5a) as prepared using a published procedure (J. Het. Chem. 1977, 14, 1385-1388). Ester (5a) may be made by cyclisation of a compound of formula (5b) (where X is O or S) in a similar manner as described in process b) for compounds of formula (4).

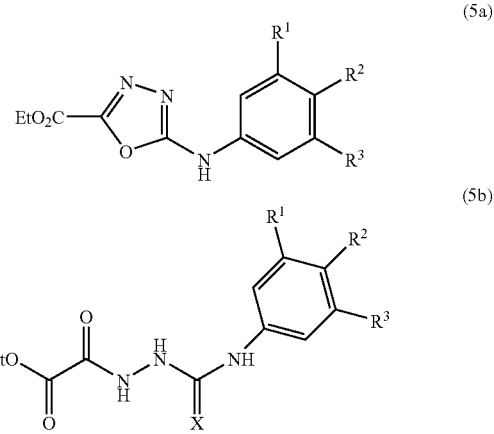

(5a)

(5b)

An alternative method for making compounds of formula (5a) is illustrated below:

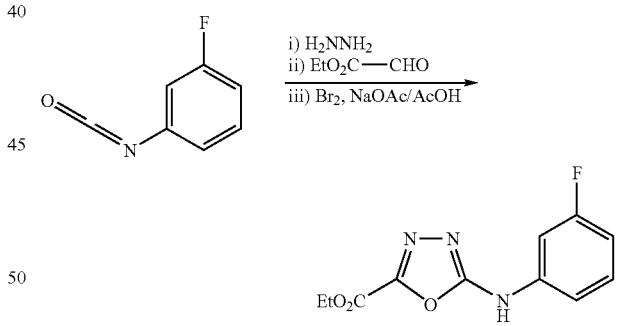

Compounds of formula (2) may be coupled with compounds of formula (3) under standard conditions for formation of amide bonds. For example using an appropriate coupling reaction, such as a carbodiimide coupling reaction performed with EDAC, optionally in the presence of DMAP, in a suitable solvent such as DCM, chloroform or DMF at room temperature.

The R group may be removed by any conditions known in the art for ester hydrolysis.

Process b)

Compounds of formula (4) and (5b) where X is S may be made by reaction of an aminocarbonyl acylhydrazine or ethoxycarbonyl acylhydrazine with a thioisocyanate or thioisocyanate equivalent such as aminothiocarbonylimidazole in a suitable solvent such as DMF or MeCN at a temperature between 0 and 100° C. The preparation of aminocarbonyl acylhydrazines from anilines and of ethoxycarbonyl acylhydrazines is well known in the art. For example reaction of an aniline with methyl chlorooxoacetate in the presence of pyridine in a suitable solvent such as DCM followed by reaction with hydrazine in a suitable solvent such as ethanol at a temperature between 0 and 100° C.

The compound of formula (4) may then be cyclised using, for example agents such as carbonyldiimidazole, or tosyl chloride and a suitable base (such as triethylamine), under conditions known in the art. The R group may be removed by any conditions known in the art for ester hydrolysis.

Iso(thio)cyanates R'—NCX (where X is O or S) are commercially available or may be made by reaction of the acid chlorides R'—NH$_2$ with for example (thio)phosgene or a (thio)phosgene equivalent followed by a suitable base (such as triethylamine).

It will be appreciated that certain of the various ring substituents in the compounds of the present invention, for example $R^1$, $R^2$ and $R^3$, may be introduced by standard aromatic substitution reactions or generated by conventional functional group modifications either prior to or immediately following the processes mentioned above, and as such are included in the process aspect of the invention. Such reactions may convert one compound of the formula (I) into another compound of the formula (I). Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkanesulfinyl or alkanesulfonyl.

If not commercially available, the necessary starting materials for the procedures such as those described above may be made by procedures which are selected from standard organic chemical techniques, techniques which are analogous to the synthesis of known, structurally similar compounds, techniques which are described or illustrated in the references given above, or techniques which are analogous to the above described procedure or the procedures described in the examples. The reader is further referred to Advanced Organic Chemistry, 5$^{th}$ Edition, by Jerry March and Michael Smith, published by John Wiley & Sons 2001, for general guidance on reaction conditions and reagents.

It will be appreciated that some intermediates to compounds of the formula (I) are also novel and these are provided as separate independent aspects of the invention. In particular, compounds of formula (4) form a further aspect of the invention. Furthermore, ester derivatives of compounds of formula (I) form a further aspect of the invention.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, John Wiley and Sons, 1991).

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

Examples of a suitable protecting group for a hydroxy group is, for example, an acyl group, for example an alkanoyl group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl or SEM may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine or 2-hydroxyethylamine, or with hydrazine.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art, or they may be removed during a later reaction step or work-up.

The skilled organic chemist will be able to use and adapt the information contained and referenced within the above references, and accompanying Examples therein and also the examples herein, to obtain necessary starting materials, and products.

The removal of any protecting groups and the formation of a pharmaceutically-acceptable salt are within the skill of an ordinary organic chemist using standard techniques. Furthermore, details on the these steps has been provided hereinbefore.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

According to a further aspect of the invention there is provided a pharmaceutical composition which comprises a compound of formula (I) as defined hereinbefore or a pharmaceutically-acceptable salt thereof, in association with a pharmaceutically-acceptable excipient or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

According to a further aspect of the present invention there is provided a compound of formula (I), (IA) and/or (IB) or a pharmaceutically acceptable salt thereof as defined hereinbefore for use in a method of treatment of the human or animal body by therapy.

We have found that compounds of the present invention inhibit DGAT1 activity and are therefore of interest for their blood glucose-lowering effects.

A further feature of the present invention is a compound of formula (I), (IA) and/or (IB) or a pharmaceutically-acceptable salt thereof for use as a medicament.

Conveniently this is a compound of formula (I), (IA) and/or (IB) or a pharmaceutically-acceptable salt thereof, for use as a medicament for producing an inhibition of DGAT1 activity in a warm-blooded animal such as a human being.

Particularly this is a compound of formula (I), (IA) and/or (IB) or a pharmaceutically-acceptable salt thereof, for use as a medicament for treating diabetes mellitus and/or obesity in a warm-blooded animal such as a human being.

Thus according to a further aspect of the invention there is provided the use of a compound of formula (I), (IA) and/or (IB) or a pharmaceutically-acceptable salt thereof in the manufacture of a medicament for use in the production of an inhibition of DGAT1 activity in a warm-blooded animal such as a human being.

Thus according to a further aspect of the invention there is provided the use of a compound of formula (I), (IA) and/or (IB) or a pharmaceutically-acceptable salt thereof in the manufacture of a medicament for use in the treatment of diabetes mellitus and/or obesity in a warm-blooded animal such as a human being.

According to a further aspect of the invention there is provided a pharmaceutical composition which comprises a compound of formula (I), (IA) and/or (IB) as defined hereinbefore or a pharmaceutically-acceptable salt thereof, in association with a pharmaceutically-acceptable excipient or carrier for use in producing an inhibition of DGAT1 activity in an warm-blooded animal, such as a human being.

According to a further aspect of the invention there is provided a pharmaceutical composition which comprises a compound of formula (I), (IA) and/or (IB) as defined hereinbefore or a pharmaceutically-acceptable salt thereof, in association with a pharmaceutically-acceptable excipient or carrier for use in the treatment of diabetes mellitus and/or obesity in an warm-blooded animal, such as a human being.

According to a further feature of the invention there is provided a method for producing an inhibition of DGAT1 activity in a warm-blooded animal, such as a human being, in need of such treatment which comprises administering to said animal an effective amount of a compound of formula (I), (IA) and/or (IB) or a pharmaceutically-acceptable salt thereof as defined hereinbefore.

According to a further feature of the invention there is provided a method of treating diabetes mellitus and/or obesity in a warm-blooded animal, such as a human being, in need of such treatment which comprises administering to said animal an effective amount of a compound of formula (I), (IA) and/or (IB) or a pharmaceutically-acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

As stated above compounds defined in the present invention are of interest for their ability to inhibit the activity of DGAT1. A compound of the invention may therefore be useful for the prevention, delay or treatment of a range of disease states including diabetes mellitus, more specifically type 2 diabetes mellitus (T2DM) and complications arising there from (for example retinopathy, neuropathy and nephropathy), impaired glucose tolerance (IGT), conditions of impaired fasting glucose, metabolic acidosis, ketosis, dysmetabolic syndrome, arthritis, osteoporosis, obesity and obesity related disorders, (which include peripheral vascular disease, (including intermittent claudication), cardiac failure and certain cardiac myopathies, myocardial ischaemia, cerebral ischaemia and reperfusion, hyperlipidaemias, atherosclerosis, infertility and polycystic ovary syndrome); the compounds of the invention may also be useful for muscle weakness, diseases of the skin such as acne, various immunomodulatory diseases (such as psoriasis), HIV infection, inflammatory bowel syndrome and inflammatory bowel disease such as Crohn's disease and ulcerative colitis.

In particular, the compounds of the present invention are of interest for the prevention, delay or treatment of diabetes mellitus and/or obesity and/or obesity related disorders. In one aspect, the compounds of the invention are used for prevention, delay or treatment of diabetes mellitus. In another aspect, the compounds of the invention are used for prevention, delay or treatment of obesity. In a further aspect, the compounds of the invention are used for prevention, delay or treatment of obesity related disorders.

The inhibition of DGAT1 activity described herein may be applied as a sole therapy or in combination with one or more other substances and/or treatments for the indication being treated. Such conjoint treatment may be achieved by way of the simultaneous, sequential or separate administration of the individual components of the treatment. Simultaneous treatment may be in a single tablet or in separate tablets. For example such conjoint treatment may be beneficial in the treatment of metabolic syndrome [defined as abdominal obesity (as measured by waist circumference against ethnic and gender specific cut-points) plus any two of the following: hypertriglyceridemia (>150 mg/dl; 1.7 mmol/l); low HDLc (<40 mg/dl or <1.03 mmol/l for men and <50 mg/dl or 1.29 mmol/l for women) or on treatment for low HDL (high density lipoprotein); hypertension (SBP$\geq$130 mmHg DBP$\geq$85 mmHg) or on treatment for hypertension; and hyperglycemia (fasting plasma glucose$\geq$100 mg/dl or 5.6 mmol/l or impaired glucose tolerance or pre-existing diabetes mellitus)—International Diabetes Federation & input from IAS/NCEP].

Such conjoint treatments may include the following main categories:
1) Anti-obesity therapies such as those that cause weight loss by effects on food intake, nutrient absorption or energy expenditure, such as orlistat, sibutramine and the like.
2) Insulin secretagogues including sulphonylureas (for example glibenclamide, glipizide), prandial glucose regulators (for example repaglinide, nateglinide);
3) Agents that improve incretin action (for example dipeptidyl peptidase IV inhibitors, and GLP-1 agonists);
4) Insulin sensitising agents including PPARgamma agonists (for example pioglitazone and rosiglitazone), and agents with combined PPARalpha and gamma activity;
5) Agents that modulate hepatic glucose balance (for example metformin, fructose 1,6 bisphosphatase inhibitors, glycogen phopsphorylase inhibitors, glycogen synthase kinase inhibitors, glucokinase activators);
6) Agents designed to reduce the absorption of glucose from the intestine (for example acarbose);
7) Agents that prevent the reabsorption of glucose by the kidney (SGLT inhibitors);
8) Agents designed to treat the complications of prolonged hyperglycaemia (for example aldose reductase inhibitors);
9) Anti-dyslipidaemia agents such as, HMG-CoA reductase inhibitors (eg statins); PPARα-agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
10) Antihypertensive agents such as, β-blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
11) Haemostasis modulators such as, antithrombotics, activators of fibrinolysis and antiplatelet agents; thrombin antagonists; factor Xa inhibitors; factor VIIa inhibitors); anti-platelet agents (eg. aspirin, clopidogrel); anticoagulants (heparin and Low molecular weight analogues, hirudin) and warfarin;
12) Agents which antagonise the actions of glucagon; and
13) Anti-inflammatory agents, such as non-steroidal anti-inflammatory drugs (eg. aspirin) and steroidal anti-inflammatory agents (eg. cortisone).

In addition to their use in therapeutic medicine, compounds of formula (I) and their pharmaceutically-acceptable salts are also useful as pharmacological tools in the development and standardisation of in vitro and in vivo test systems for the evaluation of the effects of inhibitors of DGAT1 activity in laboratory animals such as cats, dogs, rabbits, monkeys, rats and mice, as part of the search for new therapeutic agents.

As indicated above, all of the compounds, and their corresponding pharmaceutically-acceptable salts, are useful in inhibiting DGAT1. The ability of the compounds of formula (I), and their corresponding pharmaceutically-acceptable acid addition salts, to inhibit DGAT1 may be demonstrated employing the following enzyme assay:

Human Enzyme Assay

The in vitro assay to identify DGAT1 inhibitors uses human DGAT1 expressed in insect cell membranes as the enzyme source (Proc. Natl. Acad. Sci. 1998, 95, 13018-13023). Briefly, sf9 cells were infected with recombinant baculovirus containing human DGAT1 coding sequences and harvested after 48 h. Cells were lysed by sonication and membranes isolated by centrifuging at 28000 rpm for 1 h at 4° C. on a 41% sucrose gradient. The membrane fraction at the interphase was collected, washed, and stored in liquid nitrogen.

DGAT1 activity was assayed by a modification of the method described by Coleman (Methods in Enzymology 1992, 209, 98-102). Compound at 1-10 µM was incubated with 0.4 µg membrane protein, 5 mM $MgCl_2$, and 100 µM 1,2 dioleoyl-sn-glycerol in a total assay volume of 200 µl in plastic tubes. The reaction was started by adding $^{14}C$ oleoyl coenzyme A (30 µM final concentration) and incubated at room temperature for 30 minutes. The reaction was stopped by adding 1.5 mL 2-propanol:heptane:water (80:20:2). Radioactive triolein product was separated into the organic phase by adding 1 mL heptane and 0.5 mL 0.1 M carbonate buffer pH 9.5. DGAT1 activity was quantified by counting aliquots of the upper heptane layer by liquid scintillography.

Using this assay the compounds generally show activity with $IC_{50}$<10 mM, preferably <1 µM, more preferably <0.1 µM, particularly, <0.05 µM, and more particularly <0.01 µM. Example 13 showed an $IC_{50}$=0.017 µM.

The ability of the compounds of formula (I), and their corresponding pharmaceutically-acceptable acid salts, to inhibit DGAT1 may further be demonstrated employing the following whole cell assays 1) and 2):

1) Measurement of Triglyceride Synthesis in 3T3 Cells

Mouse adipocyte 3T3 cells were cultured to confluency in 6 well plates in new born calf serum containing media. Differentiation of the cells was induced by incubating in medium containing 10% foetal calf serum, 1 µg/mL insulin, 0.25 µM dexamethasone and 0.5 mM isobutylmethyl xanthine. After 48 h the cells were maintained in medium containing 10% foetal calf serum and 1 µg/mL insulin for a further 4-6 days. For the experiment, the medium was changed to serum-free medium and the cells pre-incubated with compound solubilised in DMSO (final concentration 0.1%) for 30 minutes. De novo lipogenesis was measured by the addition of 0.25 mM sodium acetate plus 1 µCi/mL $^{14}C$-sodium acetate to each well for a further 2 h (J. Biol. Chem., 1976, 251, 6462-6464). The cells were washed in phosphate buffered saline and solubilised in 1% sodium dodecyl sulfate. An aliquot was removed for protein determination using a protein estimation kit (Perbio) based on the method of Lowry (J. Biol. Chem., 1951, 193, 265-275). The lipids were extracted into the organic phase using a heptane:propan-2-ol:water (80:20:2) mixture followed by aliquots of water and heptane according to the method of Coleman (Methods in Enzymology, 1992, 209, 98-104). The organic phase was collected and the solvent evaporated under a stream of nitrogen. The extracts solubilised in iso-hexane:acetic acid (99:1) and lipids separated via normal phase high performance liquid chromatography (HPLC) using a Lichrospher diol-5, 4×250 mm column and a gradient solvent system of iso-hexane:acetic acid (99:1) and iso-hexane:propan-2-ol:acetic acid (85:15:1), flow rate of 1 mL/minute according to the method of Silversand and Haux (1997). Incorporation of radiolabel into the triglyceride fraction was analysed using a Radiomatic Flo-one Detector (Packard) connected to the HPLC machine.

2) Measurement of Triglyceride Synthesis in MCF7 Cells

Human mammary epithelial (MCF7) cells were cultured to confluency in 6 well plates in foetal calf serum containing media. For the experiment, the medium was changed to serum-free medium and the cells pre-incubated with compound solubilised in DMSO (final concentration 0.1%) for 30 minutes. De novo lipogenesis was measured by the addition of 50 µM sodium acetate plus 3 µCi/mL $^{14}C$-sodium acetate to each well for a further 3 h (J. Biol. Chem., 1976, 251, 6462-6464). The cells were washed in phosphate buffered saline and solubilised in 1% sodium dodecyl sulfate. An aliquot was removed for protein determination using a protein estimation kit (Perbio) based on the method of Lowry (J. Biol. Chem., 1951, 193, 265-275). The lipids were extracted into the organic phase using a heptane:propan-2-ol:water (80:20:2) mixture followed by aliquots of water and heptane according to the method of Coleman (Methods in Enzymology, 1992, 209, 98-104). The organic phase was collected and the solvent evaporated under a stream of nitrogen. The extracts solubilised in iso-hexane:acetic acid (99:1) and lipids separated via normal phase high performance liquid chromatography (HPLC) using a Lichrospher diol-5, 4×250 mm column and a gradient solvent system of iso-hexane:acetic acid (99:1) and iso-hexane:propan-2-ol:acetic acid (85:15:1), flow rate of 1 mL/minute according to the method of Silversand and Haux (J. Chromat. B, 1997, 703, 7-14). Incorporation of radiolabel into the triglyceride fraction was analysed using a Radiomatic Flo-one Detector (Packard) connected to the HPLC machine.

3) The ability of compounds to inhibit ACAT can be measured using a modification of the enzyme assay described in Billheimer (1985) Methods in Enzymology, 111, 286-293. The test assesses the ability of a test compound to inhibit the esterification of cholesterol by measuring the amount of radiolabeled cholesteryl oleate formed from radiolabeled oleoyl CoA. Compound was incubated with 10 μg membrane protein and 267 μM cholesterol. After a 5 minute pre-incubation at 37° C. the reaction was started by adding $^{14}C$ oleoyl coenzyme A (50 μM final concentration) and incubated at 37° C. for a further 30 minutes. The reaction was stopped by adding 2-propanol:heptane (12:1). Radioactive cholesteryl ester product was separated into the organic phase by adding heptane and 1M carbonate buffer pH 9.5. ACAT activity was quantified by counting aliquots of the upper heptane layer by liquid scintillography.

The selectivity of a compound to inhibit DGAT over inhibition of ACAT may be defined as the ratio of IC50 values generated in the DGAT and ACAT enzyme assays for a particular compound. For example, Example 13 demonstrated 310 fold selectivity.

In the above other pharmaceutical composition, process, method, use and medicament manufacture features, the alternative and preferred embodiments of the compounds of the invention described herein also apply.

EXAMPLES

The invention will now be illustrated by the following Examples in which, unless stated otherwise:
(i) temperatures are given in degrees Celsius (° C.); operations were carried out at room or ambient temperature, that is, at a temperature in the range of 18-25° C. and under an atmosphere of an inert gas such as argon;
(ii) organic solutions were dried over anhydrous magnesium sulfate; evaporation of solvent was carried out using a rotary evaporator under reduced pressure (600-4000 Pa; 4.5-30 mmHg) with a bath temperature of up to 60° C.;
(iii) chromatography means flash chromatography on silica gel; where a Biotage cartridge is referred to this means a cartridge containing KP-SIL™ silica, 60 Å, particle size 32-63 mM, supplied by Biotage, a division of Dyax Corp., 1500 Avon Street Extended, Charlottesville, Va. 22902, USA;
(iv) in general, the course of reactions was followed by TLC and reaction times are given for illustration only;
(v) yields are given for illustration only and are not necessarily those which can be obtained by diligent process development; preparations were repeated if more material was required;
(vi) where given, NMR data ($^1H$) is in the form of delta values for major diagnostic protons, given in parts per million (ppm) relative to tetramethylsilane (TMS), determined at 300 or 400 MHz (unless otherwise stated) using perdeuterio dimethyl sulfoxide (DMSO-$d_6$) as solvent, unless otherwise stated; peak multiplicities are shown thus: s, singlet; d, doublet; dd, doublet of doublets; dt, doublet of triplets; dm, doublet of multiplets; t, triplet, q, quartet; m, multiplet; br, broad;
(vii) chemical symbols have their usual meanings; SI units and symbols are used;
(viii) solvent ratios are given in volume:volume (v/v) terms;
(ix) mass spectra (MS) (loop) were recorded on a Micromass Platform LC equipped with HP 1100 detector; unless otherwise stated the mass ion quoted is ($MH^+$);
(x) LCMS (liquid chromatography-mass spectrometry) were recorded on a system comprising Waters 2790 LC equipped with a Waters 996 Photodiode array detector and Micromass ZMD MS, using a Phenomenex® Gemini 5u C18 110A 50×2 mm column and eluting with a flow rate of 1.1 ml/min with 5% (Water/Acetonitrile (1:1)+1% formic acid) and a gradient increasing from 0-95% of acetonitrile over the first 4 minutes, the balance (95-0%) being water and where HPLC Retention Times are reported these are in minutes in this system unless otherwise stated; unless otherwise stated the mass ion quoted is ($MH^+$);
(xi) where phase separation cartridges are stated then ISOLUTE Phase Separator 70 ml columns, supplied by Argonaut Technologies, New Road, Hengoed, Mid Glamorgan, CF82 8AU, United Kingdom, were used;
(xii) where a SiliCycle cartridge is referred to this means a cartridge containing Ultra Pure Silica Gel particle size 230-400 mesh, 40-63 um pore size, supplied by SiliCycle Chemical Division, 1200 Ave St-Jean-Baptiste, Suite 114, Quebec City, Quebec, G2E 5E8, CANADA;
(xiii) where an Isco Companion is referred to then a Combiflash companion chromatography instrument, supplied by ISOC Inc. Address Teledyne ISOC Inc, 4700 Superior Street, Lincoln, Nebr. 68504, USA, was used;
(xiv) where a microwave is referred to this means a Biotage Initiator sixty or Smith Creator microwave, supplied by Biotage, a division of Dyax Corp., 1500 Avon Street Extended, Charlottesville, Va. 22902, USA;
(xv) where GCMS is referred to then a Gas Chromatography—Mass Spectrometry analysis was carried out on a QP-2010 GC-MS system fitted with an AOC 20i autosampler and controlled by 'GCMS solutions' software, version 2.0, supplied by Shimadzu, Milton Keynes, MK12 5RE, UK; the GC column was a DB-5MS of length 25 m, 0.32 mm i.d. with a film thickness of 0.52 μm supplied by J & W Scientific, Folsom, Calif., USA;
(xvi) where a centrifuge is referred to this means a Genevac EZ-2plus, supplied by Genevac Limited, The Soveriegn Centre, Farthing Road, Ipswich, IP1 5AP, UK;
(xvii) where chiral chromatography is referred to this is carried generally out using a 20 μm Merck 50 mm Chiralpak AD column, (Chiral Stationary Phase supplied by Chiral Technologies Europe, Parc d'Innovation, Bd. Gonthier d'Andernach, 67404 Illkirch Cedex, France), using MeCN/2-propanol/AcOH (90/10/0.1) as eluent, flow rate 80 mL/min, wavelength 300 nm, using a Gilson prep HPLC instrument (200 ml heads);
(xviii) melting points were determined using a Buchi 530 apparatus and are uncorrected;
(xix) The following abbreviations may be used below or in the process section hereinbefore:
  $Et_2O$ or ether diethyl ether
  DMF dimethylformamide
  DCM dichloromethane
  DME 1,2-dimethoxyethane MeOH methanol
EtOH ethanol
H₂O water
TFA trifluoroacetic acid
THF tetrahydrofuran
DMSO dimethylsulfoxide
HOBt 1-hydroxybenzotriazole
EDCI (EDAC) 1-ethyl-3-(3-dimethylaminopropyl)carbo-
diimide hydrochloride
DIPEA diisopropylethylamine
DEAD diethyl azodicarboxylate
EtOAc ethyl acetate
NaHCO₃ sodium bicarbonate/sodium hydrogencarbonate
K₃PO₄ potassium phosphate
PS polymer supported
BINAP 2,2'-bis(diphenylphosphino)-1,1'binaphthyl
Dppf 1,1'-bis(diphenylphosphino)ferrocene
dba dibenzylidineacetone
PS-CDI polymer supported carbonyldiimidazole
CH₃CN or MeCN acetonitrile
h hour
min minute
HATU O-(7-Azabenzotriazol-1-yl)-N,N,N',N'-tetram-
ethyluronium hexofluorophosphate
NaOH sodium hydroxide
AcOH acetic acid
DMA dimethyl acetamide
nBuLi n-butyl lithium
MgSO₄ magnesium sulfate
Na₂SO₄ sodium sulfate
CDCl₃ deutero chloroform
CD₃OD per-deuterated methanol
Boc tert-butoxycarbonyl
HCl hydrochloric acid
All final compound names were derived using ACD NAME computer package.

Example 1 cis-4-{4-[({5-[(3,4-Difluorophenyl)amino]-1,3,4-oxadiazol-2-yl}carbonyl)amino]-phenoxy}cyclohexanecarboxylic acid

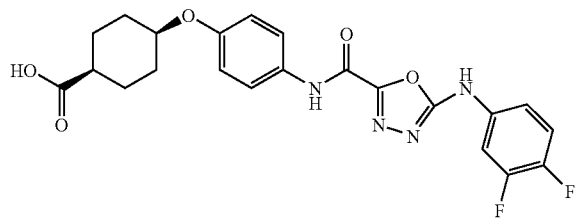

Ethyl cis-4-(4-{[hydrazino(oxo)acetyl]amino}phenoxy)cyclohexanecarboxylate (Intermediate 1, 698 mg, 2.00 mmol) was added in one portion to a stirred solution of 3,4-difluorophenyl isothiocyanate (411 mg, 2.40 mmol) in DMF (10 mL) and the reaction mixture was stirred at 65° C. for 30 mins. EDCI (461 mg, 2.40 mmol) was added in one portion and the reaction mixture was heated to 85° C. for 3 h. The mixture was cooled to ambient temperature and water (15 mL) was added and the resulting suspension was filtered to leave a cream solid. The solid was taken up in a mixture of MeOH (8 mL) and THF (4 mL) and a 2N aqueous solution of NaOH (4 mL) was added in one portion and the reaction mixture was stirred at ambient temperature for 16 h. The reaction mixture was acidified by the addition of 2M HCl and the resulting precipitate was filtered, washed with water (10 mL) and dried under high vacuum to leave a solid. The solid was recrystallised from refluxing glacial acetic acid to give the title compound as a white solid (428 mg, 47%).

¹H NMR δ1.60-1.86 (m, 8H), 2.32-2.42 (m, 1H), 4.51 (s, 1H), 6.96 (d, 2H), 7.31-7.38 (m, 1H), 7.49 (q, 1H), 7.66-7.75 (m, 3H), 10.97 (s, 1H), 11.27 (s, 1H), 12.12 (s, 1H); MS m/e MH⁺ 459.

Example 2 cis-4-(4-{[(5-{[3-Fluoro-5-(trifluoromethyl)phenyl]amino}-1,3,4-oxadiazol-2-yl)carbonyl]amino}phenoxy)cyclohexanecarboxylic acid

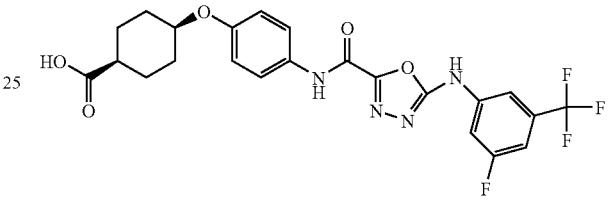

Sodium hydride (60% dispersion in mineral oil, 192 mg, 4.80 mmol) was added to a stirred solution of 3-amino-5-fluorobenzotrifluoride (430 mg, 2.40 mmol) in DMF (10 mL) at ambient temperature. After 5 mins di-2-pyridyl thionocarbonate (557 mg, 2.40 mmol) was added in one portion and stirring was continued for 10 mins. Ethyl cis-4-(4-{[hydrazino(oxo)acetyl]amino}phenoxy)cyclohexanecarboxylate (Intermediate 1, 698 mg, 2.00 mmol) was added in one portion to the reaction mixture and stirred at 65° C. for 30 mins. EDCI (460 mg, 2.40 mmol) was then added in one portion and the reaction mixture was heated to 85° C. for 3 h. The mixture was cooled to ambient temperature and water (15 mL) was added and the resulting suspension was filtered to leave a cream solid. The solid was taken up in a mixture of MeOH (8 mL) and THF (4 mL) and a 2N aqueous solution of NaOH (4 mL) was added in one portion and the reaction mixture was stirred at ambient temperature for 16 h. The reaction mixture was acidified by the addition of 2M HCl and the resulting precipitate was filtered, washed with water (10 mL) and dried under high vacuum to leave a solid. The solid was recrystallised from refluxing glacial acetic acid to provide the title compound as a white solid (448 mg, 44%).

¹H NMR δ1.59-1.87 (m, 8H), 2.31-2.43 (m, 1H), 4.51 (s, 1H), 6.96 (d, 2H), 7.37 (d, 1H), 7.69 (d, 2H), 7.73-7.82 (m, 2H), 11.01 (s, 1H), 11.69 (s, 1H), 12.11 (s, 1H); MS m/e MH⁺ 509.

Examples 3-9

The following compounds were made using commercially available isothiocyanates by the method described in Example 1.

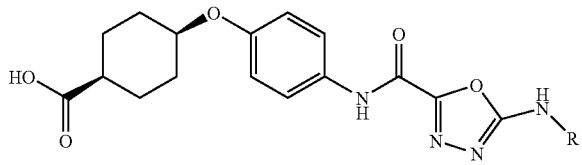

| Example | R | ¹H NMR δ | MS m/e MH⁺ |
|---|---|---|---|
| 3 | 4-tBu-3-Cl-benzonitrile (via CN, Cl substituted phenyl) | ¹H NMR δ 1.59-1.86 (m, 8 H), 2.31-2.42 (m, 1 H), 4.51 (s, 1 H), 6.96 (d, 2 H), 7.63-7.74 (m, 3 H), 7.93 (d, 1 H), 8.00 (d, 1 H), 11.03 (s, 1 H), 11.87 (s, 1 H), 12.13 (s, 1 H) | 482 |
| 4 | 4-(trifluoromethoxy)phenyl | ¹H NMR δ 1.45-1.71 (m, 8 H), 2.17-2.27 (m, 1 H), 4.36 (s, 1 H), 6.81 (d, 2 H), 7.28 (d, 2 H), 7.50-7.59 (m, 4 H), 10.81 (s, 1 H), 11.08 (s, 1 H), 11.98 (s, 1 H) | 507 |
| 5 | 3,4,5-trifluorophenyl | ¹H NMR δ 1.59-1.87 (m, 8 H), 2.32-2.43 (m, 1 H), 4.51 (s, 1 H), 6.96 (d, 2 H), 7.42-7.53 (m, 2 H), 7.69 (d, 2 H), 10.99 (s, 1 H), 11.50 (s, 1 H), 12.10 (s, 1 H) | 477 |
| 6 | 4-cyanophenyl | ¹H NMR δ 1.45-1.72 (m, 8 H), 2.17-2.28 (m, 1 H), 4.37 (s, 1 H), 6.82 (d, 2 H), 7.55 (d, 2 H), 7.63 (d, 2 H), 7.74 (d, 2 H), 10.87 (s, 1 H), 11.48 (s, 1 H), 11.96 (s, 1 H) | 448 |
| 7 | 4-fluorophenyl | ¹H NMR δ 1.60-1.86 (m, 8 H), 2.32-2.43 (m, 1 H), 4.50 (s, 1 H), 6.95 (d, 2 H), 7.25 (t, 2 H), 7.58-7.65 (m, 2 H), 7.69 (d, 2 H), 10.94 (s, 1 H), 11.03 (s, 1 H), 12.11 (s, 1 H) | 441 |
| 8 | 4-(difluoromethoxy)phenyl | ¹H NMR δ 1.58-1.86 (m, 8 H), 2.31-2.43 (m, 1 H), 4.51 (s, 1 H), 6.95 (d, 2 H), 7.24 (d, 2 H), 7.62 (d, 2 H), 7.70 (d, 2 H), 10.94 (s, 1 H), 11.08 (s, 1 H), 12.12 (s, 1 H) | 489 |
| 9 | 3-cyanophenyl | ¹H NMR δ 1.58-1.87 (m, 8 H), 2.30-2.43 (m, 1 H), 4.51 (s, 1 H), 6.95 (d, 2 H), 7.54 (d, 1 H), 7.63 (t, 1 H), 7.70 (d, 2 H), 7.86 (d, 1 H), 8.02 (s, 1 H), 10.99 (s, 1 H), 11.46 (s, 1 H), 12.10 (s, 1 H) | 448 |

Examples 10-11

The following compounds were made using commercially available anilines by the method described in Example 2.

| Example | R | $^1$H NMR δ | MS m/e MH$^+$ |
|---|---|---|---|
| 10 | (4-tert-butyl-2-(trifluoromethyl)phenyl with nitrile) | $^1$H NMR δ 1.57-1.88 (m, 8 H), 2.31-2.43 (m, 1 H), 4.51 (s, 1 H), 6.96 (d, 2 H), 7.69 (d, 2 H), 8.01 (d, 1 H), 8.11-8.24 (m, 2 H), 11.04 (s, 1 H), 12.03 (s, 1 H), 12.14 (s, 1 H) | 516 |
| 11 | (3-tert-butyl phenyl with difluoromethoxy) | $^1$H NMR δ 1.55-1.91 (m, 8 H), 2.30- 2.43 (m, 1 H), 4.39-4.56 (m, 1 H), 6.82-7.76 (m, 8 H), 10.97 (s, 1 H), 11.24 (s, 1 H), 12.07 (s, 1 H) | 489 |

Example 12 trans-4-(4-{[(5-{[4-(Difluoromethoxy)phenyl]amino}-1,3,4-oxadiazol-2-yl)carbonyl]amino}phenoxy)cyclohexanecarboxylic acid

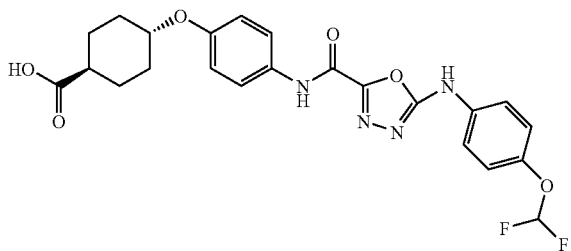

Ethyl trans-4-(4-{[hydrazino(oxo)acetyl]amino}phenoxy)cyclohexanecarboxylate (Intermediate 3, 698 mg, 2.00 mmol) was added in one portion to a stirred solution of 4-(difluoromethoxy)phenyl isothiocyanate (483 mg, 2.40 mmol) in DMF (10 mL) and the reaction mixture was stirred at 65° C. for 30 mins. EDCI (461 mg, 2.40 mmol) was added in one portion and the reaction mixture was heated to 85° C. for 3 h. The mixture was cooled to ambient temperature and water (15 mL) was added and the resulting suspension was filtered to provide a cream solid. The solid was taken up in a mixture of MeOH (8 mL) and THF (4 mL) and a 2N aqueous solution of NaOH (4 mL) was added in one portion and the reaction mixture was stirred at ambient temperature for 16 h. The reaction mixture was acidified by the addition of a 2M aqueous solution of HCl and the resulting precipitate was filtered, washed with water (10 mL) and dried under high vacuum to leave a solid. The solid was recrystallised from refluxing glacial acetic acid to give the title compound as a white solid (392 mg, 40%).

$^1$H NMR δ 1.31-1.59 (m, 4H), 1.87-1.99 (m, 2H), 2.01-2.11 (m, 2H), 2.20-2.31 (m, 1H), 4.23-4.33 (m, 1H), 6.94 (d, 2H), 7.17 (t, 1H), 7.24 (d, 2H), 7.63 (d, 2H), 7.70 (d, 2H), 10.94 (s, 1H), 11.08 (s, 1H), 12.07 (s, 1H); MS m/e MH$^+$ 489.

Examples 13-17

The following compounds were synthesised using commercially available isothiocyanates by the method described in Example 12.

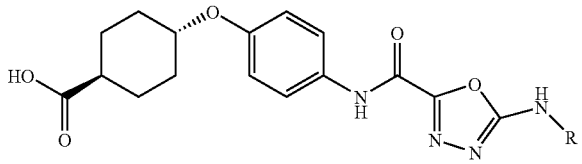

| Example | R | $^1$H NMR δ | MS m/e MH$^+$ |
|---|---|---|---|
| 13 | ![4-fluorophenyl] | $^1$H NMR δ 1.31-1.58 (m, 4 H), 1.89-1.99 (m, 2 H), 2.01-2.11 (m, 2 H), 2.19-2.31 (m, 1 H), 4.21-4.33 (m, 1 H), 6.94 (d, 2 H), 7.26 (t, 2 H), 7.58-7.65 (m, 2 H), 7.69 (d, 2 H), 10.94 (s, 1 H), 11.04 (s, 1 H), 12.12 (s, 1 H) | 441 |
| 14 | ![3-cyanophenyl] | $^1$H NMR δ 1.31-1.57 (m, 4 H), 1.89-1.99 (m, 2 H), 2.01-2.12 (m, 2 H), 2.20-2.31 (m, 1 H), 4.22-4.33 (m, 1 H), 6.95 (d, 2 H), 7.54 (d, 1 H), 7.62 (t, 1 H), 7.70 (d, 2 H), 7.86 (d, 1 H), 8.02 (s, 1 H), 11.00 (s, 1 H), 11.47 (s, 1 H), 12.14 (s, 1 H) | 448 |
| 15 | ![4-cyanophenyl] | $^1$H NMR δ 1.31-1.59 (m, 4 H), 1.87-1.99 (m, 2 H), 2.01-2.11 (m, 2 H), 2.20-2.31 (m, 1 H), 4.22-4.34 (m, 1 H), 6.96 (d, 2 H), 7.69 (d, 2 H), 7.73-7.82 (m, 2 H), 7.89 (d, 2 H), 11.01 (s, 1 H), 11.62 (s, 1 H), 12.14 (s, 1 H) | 448 |
| 16 | ![4-(trifluoromethoxy)phenyl] | $^1$H NMR δ 1.30-1.58 (m, 4 H), 1.87-2.00 (m, 2 H), 2.01-2.12 (m, 2 H), 2.20-2.31 (m, 1 H), 4.22-4.34 (m, 1 H), 6.95 (d, 2 H), 7.43 (d, 2 H), 7.65-7.75 (m, 4 H), 10.97 (s, 1 H), 11.24 (s, 1 H), 12.08 (s, 1 H) | 507 |
| 17 | ![3,4-difluorophenyl] | $^1$H NMR δ 1.31-1.58 (m, 4 H), 1.86-1.99 (m, 2 H), 2.01-2.12 (m, 2 H), 2.20-2.31 (m, 1 H), 4.22-4.33 (m, 1 H), 6.95 (d, 2 H), 7.30-7.39 (m, 1 H), 7.50 (q, 1 H), 7.65-7.78 (m, 3 H), 10.97 (s, 1 H), 11.29 (s, 1 H), 12.11 (s, 1 H) | 459 |

Intermediate 1

Ethyl cis-4-(4-{[hydrazino(oxo)acetyl]amino}phenoxy)cyclohexane-carboxylate i) Ethyl cis-4-(4-nitrophenoxy)cyclohexanecarboxylate

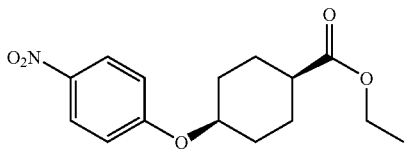

Sodium hydride (60% dispersion in mineral oil, 4.39 g, 109.7 mmol) was added in portions over 1 min to a stirred solution of ethyl 4-hydroxycyclohexanecarboxylate (18 g, 104.5 mmol) and 1-fluoro-4-nitrobenzene (11.1 mL, 109.7 mmol) in DMF (200 mL) at 0° C. under a nitrogen atmosphere. The reaction mixture was stirred at 0° C. for 5 mins and then warmed to ambient temperature and stirred for 2 h. Water (750 mL) and EtOAc (300 mL) were then added and the layers were separated. The aqueous layer was extracted with EtOAc (2×300 mL) and the combined organic layers were washed with brine (100 mL), dried (MgSO$_4$) and concentrated in vacuo to leave a residue. The crude residue was purified by column chromatography, using a gradient of 10-40% EtOAc in isohexane as eluent, to give the title compound as a yellow oil (6.95 g, 23.7 mmol, 23%).

$^1$H NMR δ 1.15-1.23 (m, 3H), 1.65-1.90 (m, 8H), 2.45-2.54 (m, 1H), 4.08 (q, 2H), 4.72-4.79 (m, 1H), 7.16 (d, 2H), 8.18 (d, 2H).

The corresponding trans-cyclohexyl isomer, ethyl trans-4-(4-nitrophenoxy)cyclohexane-carboxylate (Intermediate 2) was also isolated from this reaction as a white solid (5.50 g, 18%).

$^1$H NMR (CDCl$_3$) δ1.19 (t, 3H), 1.40-1.64 (m, 4H), 2.00-2.16 (m, 4H), 2.24-2.36 (m, 1H), 4.07 (q, 2H), 4.23-4.32 (m, 1H), 6.84 (d, 2H), 8.11 (d, 2H).

ii) Ethyl cis-4-(4-aminophenoxy)cyclohexanecarboxylate

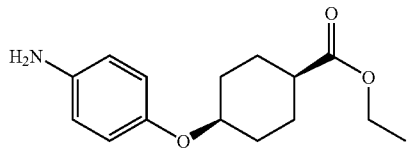

Palladium (10 wt. %) on carbon (200 mg) was added in one portion to a solution of ethyl 4-(4-nitrophenoxy)cyclohexanecarboxylate (6.95 g, 23.7 mmol) in EtOH (200 mL) and the reaction mixture was stirred under a hydrogen atmosphere at ambient temperature for 16 h. The reaction mixture was filtered and concentrated in vacuo to leave the title compound as a yellow oil (6.24 g, 100%).
$^1$H NMR δ1.19 (t, 3H), 1.53-1.67 (m, 4H), 1.71-1.85 (m, 4H), 2.37-2.46 (m, 1H), 4.08 (q, 2H), 4.19-4.26 (m, 1H), 4.58 (s, 2H), 6.50 (d, 2H), 6.66 (d, 2H); MS m/e MH$^+$ 264.

iii) Ethyl cis-4-(4-{[methoxy(oxo)acetyl]amino}phenoxy)cyclohexanecarboxylate

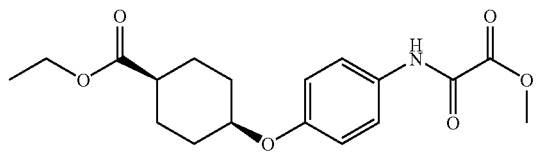

Methyl chloroooxoacetate (2.41 mL, 26.1 mmol) was added dropwise over 2 mins to a stirred solution of ethyl cis-4-(4-aminophenoxy)cyclohexanecarboxylate (6.24 g, 23.7 mmol) and diisopropylethylamine (8.25 mL, 47.4 mmol) in DCM (200 mL) and the reaction mixture was stirred at ambient temperature for 16 h. Water (75 mL) was added and the layers were separated. The organic layer was washed with an aqueous solution of hydrochloric acid (1M, 75 mL) and then a saturated aqueous solution of sodium hydrogen carbonate (75 mL), dried (MgSO$_4$) and concentrated in vacuo to provide the title compound as a white solid (8.23 g, 100%).
$^1$NMR δ1.18 (t, 3H), 1.60-1.85 (m, 8H), 2.38-2.50 (m, 1H), 3.84 (s, 3H), 4.07 (q, 2H), 4.47-4.54 (m, 1H), 6.93 (d, 2H), 7.63 (d, 2H), 10.70 (s, 1H); MS m/e (M-H)$^-$ 348.

iv) Ethyl cis-4-(4-{[hydrazino(oxo)acetyl]amino}phenoxy)cyclohexanecarboxylate

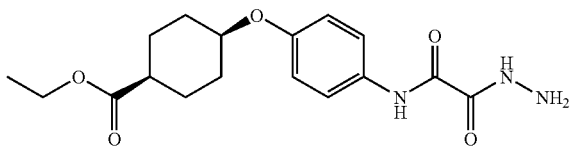

Hydrazine monohydrate (2.29 mL, 47.1 mmol) was added in one portion to a stirred solution of ethyl cis-4-(4-{[methoxy(oxo)acetyl]amino}phenoxy)cyclohexanecarboxylate (8.23 g, 23.6 mmol) in EtOH (200 mL) and the reaction mixture was stirred at 70° C. for 1 h. After cooling to ambient temperature the mixture was filtered and washed with ether (200 mL) to leave the title compound (Intermediate 1) as a white solid (7.80 g, 95%) that was used with no further purification.
$^1$H NMR δ1.18 (t, 3H), 1.59-1.86 (m, 8H), 2.41-2.49 (m, 1H), 4.07 (q, 2H), 4.50 (s, 1H), 4.60 (s, 2H), 6.93 (d, 2H), 7.71 (d, 2H), 10.23 (s, 1H), 10.49 (s, 1H).

Intermediate 3

Ethyl trans-4-(4-{[hydrazino(oxo)acetyl]amino}phenoxy)-cyclohexane-carboxylate

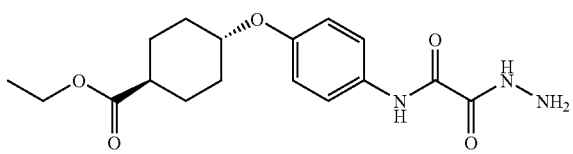

Intermediate 3 was synthesised using the reaction conditions described for Intermediate 1, starting from Intermediate 2, described in the reaction conditions for Intermediate 1(i).
$^1$H NMR δ1.17 (t, 3H), 1.32-1.57 (m, 4H), 1.89-1.97 (m, 2H), 2.00-2.09 (m, 2H), 2.29-2.39 (m, 1H), 4.05 (q, 2H), 4.22-4.31 (m, 1H), 4.60 (s, 2H), 6.92 (d, 2H), 7.70 (d, 2H), 10.23 (s, 1H), 10.48 (s, 1H); MS m/e MH$^+$ 350.

The invention claimed is:
1. A compound of formula (I):

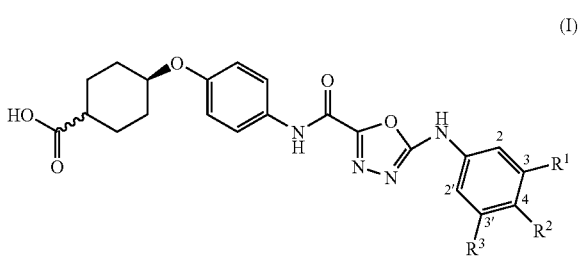

or a salt thereof, wherein:
R$^1$, R$^2$ and R$^3$ are each independently selected from hydrogen, fluoro, chloro, cyano, trifluoromethyl, trifluoromethoxy and difluoromethoxy.

2. The compound of formula (I) as claimed in claim 1, or a salt thereof, which is a compound of formula (IA):

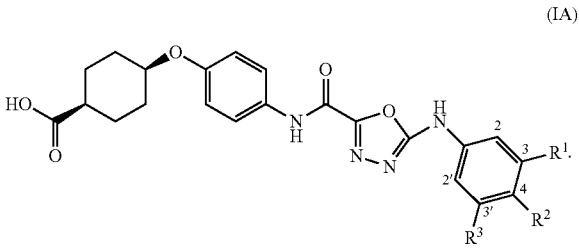

3. The compound of formula (I) as claimed in claim 1, or a salt thereof, which is a compound of formula (IB):

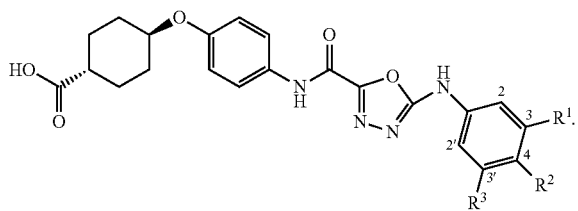

(IB)

4. The compound as claimed in claim 1, or a salt thereof wherein $R^2$ is selected from fluoro, chloro, cyano, trifluoromethyl, trifluoromethoxy and difluoromethoxy.

5. The compound as claimed in claim 4, or a salt thereof, wherein $R^2$ is selected from fluoro, trifluoromethoxy and difluoromethoxy.

6. The compound as claimed in claim 5, or a salt thereof, wherein $R^2$ is fluoro.

7. The compound as claimed in claim 1, or a salt thereof, wherein $R^1$ is hydrogen or fluoro.

8. The compound as claimed in claim 1, or a salt thereof, wherein $R^3$ is hydrogen or fluoro.

9. The compound as claimed in claim 1 which is selected from cis-4-{4-[({5-[(3,4-difluorophenyl)amino]-1,3,4-oxadiazol-2-yl}carbonyl)amino]-phenoxy}cyclohexanecarboxylic acid;

cis-4-{4-[({5-[(3-chloro-4-cyanophenyl)amino]-1,3,4-oxadiazol-2-yl}carbonyl)amino]phenoxy}cyclohexanecarboxylic acid;

cis-4-(4-{[(5-{[4-(trifluoromethoxy)phenyl]amino}-1,3,4-oxadiazol-2-yl)carbonyl]amino}phenoxy)cyclohexanecarboxylic acid;

cis-4-(4-{[(5-{[3-fluoro-5-(trifluoromethyl)phenyl]amino}-1,3,4-oxadiazol-2-yl)carbonyl]amino}phenoxy)cyclohexanecarboxylic acid;

cis-4-{4-[({5-[(3,4,5-trifluorophenyl)amino]-1,3,4-oxadiazol-2-yl}carbonyl)amino]phenoxy}cyclohexanecarboxylic acid;

cis-4-{4-[({5-[(4-cyanophenyl)amino]-1,3,4-oxadiazol-2-yl}carbonyl)amino]phenoxy}cyclohexanecarboxylic acid;

cis-4-{4-[({5-[(4-fluorophenyl)amino]-1,3,4-oxadiazol-2-yl}carbonyl)amino]phenoxy}cyclohexanecarboxylic acid;

cis-4-(4-{[(5-{[4-cyano-3-(trifluoromethyl)phenyl]amino}-1,3,4-oxadiazol-2-yl)carbonyl]amino}phenoxy)cyclohexanecarboxylic acid;

cis-4-(4-{[(5-{[3-(difluoromethoxy)phenyl]amino}-1,3,4-oxadiazol-2-yl)carbonyl]amino}phenoxy)cyclohexanecarboxylic acid;

cis-4-(4-{[(5-{[4-(difluoromethoxy)phenyl]amino}-1,3,4-oxadiazol-2-yl)carbonyl]amino}phenoxy)cyclohexanecarboxylic acid;

cis-4-{4-[({5-[(3-cyanophenyl)amino]-1,3,4-oxadiazol-2-yl}carbonyl)amino]phenoxy}cyclohexanecarboxylic acid;

trans-4-(4-{[(5-{[4-(difluoromethoxy)phenyl]amino}-1,3,4-oxadiazol-2-yl)carbonyl]-amino}phenoxy)cyclohexanecarboxylic acid;

trans-4-{4-[({5-[(4-fluorophenyl)amino]-1,3,4-oxadiazol-2-yl}carbonyl)amino]phenoxy}cyclohexanecarboxylic acid;

trans-4-{4-[({5-[(3-cyanophenyl)amino]-1,3,4-oxadiazol-2-yl}carbonyl)amino]phenoxy}cyclohexanecarboxylic acid;

trans-4-{4-[({5-[(4-cyanophenyl)amino]-1,3,4-oxadiazol-2-yl}carbonyl)amino]phenoxy}cyclohexanecarboxylic acid;

trans-4-(4-{[(5-{[4-(trifluoromethoxy)phenyl]amino}-1,3,4-oxadiazol-2-yl)carbonyl]amino}phenoxy)cyclohexanecarboxylic acid; and trans-4-{4-[({5-[(3,4-difluorophenyl)amino]-1,3,4-oxadiazol-2-yl}carbonyl)amino]phenoxy}cyclohexanecarboxylic acid;

or a pharmaceutically-acceptable salt of any of these.

10. A pharmaceutical composition comprising a compound of formula (I) as claimed in claim 1 or a pharmaceutically-acceptable salt thereof, in association with a pharmaceutically-acceptable excipient or carrier.

11. A method for producing an inhibition of DGAT1 activity in a warm-blooded animal in need thereof comprising administering to said animal an effective amount of a compound of formula (I) as claimed in claim 1 or a pharmaceutically-acceptable salt thereof.

12. A method of treating diabetes mellitus and/or obesity in a warm-blooded animal suffering from said diabetes mellitus and/or obesity comprising administering to said animal an effective amount of a compound of formula (I) as claimed in claim 1 or a pharmaceutically-acceptable salt thereof.

13. A process for preparing a compound according to claim 1, or a salt thereof comprising one of the following steps a) or b) (wherein all variables are as hereinbefore defined for a compound of formula (I) unless otherwise stated):

a) reacting an amine of formula (2) with a carboxylate salt of formula (3), wherein R is (1-6C)alkyl followed by hydrolysis of the R group

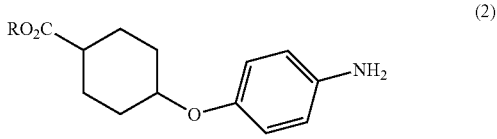

(2)

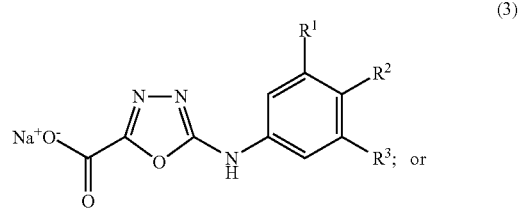

(3)

b) cyclising a compound of formula (4) wherein X is O and wherein R is (1-6C)alkyl, followed by hydrolysis of the R group

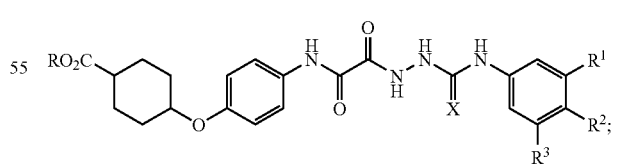

(4)

and optionally thereafter:
1) removing any protecting groups; and/or
2) forming a salt.

* * * * *

UNITED STATES PATENT AND TRADEMARK OFFICE
CERTIFICATE OF CORRECTION

PATENT NO. : 8,084,478 B2  Page 1 of 1
APPLICATION NO. : 12/302185
DATED : December 27, 2011
INVENTOR(S) : Roger John Butlin and Alleyn Thomas Plowright It is certified that error appears in the above-identified patent and that said Letters Patent is hereby corrected as shown below:

On the Title Page:

Item (73) Assignee: "AsstraZeneca AB, Sodertalje (SE)" should be changed to
--AstraZeneca AB, Sodertalje (SE)--

Signed and Sealed this
Fourteenth Day of February, 2012

David J. Kappos
*Director of the United States Patent and Trademark Office*